US00PP11129P

United States Patent [19]

Roberson

[11] Patent Number: Plant 11,129

[45] Date of Patent: Nov. 23, 1999

[54] *CANNA GENERALIS* PLANT NAMED 'ROBLIBKEY'

[76] Inventor: Robert J. Roberson, 31706 E. Pink Hill Rd., Grain Valley, Jackson County, Mo. 64029

[21] Appl. No.: 08/987,612

[22] Filed: Dec. 9, 1997

[51] Int. Cl.[6] ..... A01H 5/00

[52] U.S. Cl. ..... Plt./263

[58] Field of Search ..... Plt./68.1, 263

*Primary Examiner*—Howard J. Locker
*Assistant Examiner*—Ashwin Mehta
*Attorney, Agent, or Firm*—Rothwell, Figg, Ernst & Kurz

[57] ABSTRACT

This invention relates to a new and distinct *Canna generalis* cultivar which is outstanding because of its compact dwarf growth habit, its pastel yellow color with lime-green hue, its long-term bloom display, its apple green foliage edged with white margins, its large, healthy rhizomes, and its ultra dwarf early bloom display.

1 Drawing Sheet

SUMMARY OF THE INVENTION

This invention relates to a new and distinct Canna cultivar which is outstanding because of its compact dwarf growth habit, its pastel yellow color with lime-green hue, its long-term bloom display, its apple green foliage edged with white margins, its large, healthy rhizomes, and its ultra dwarf early bloom display. This selection was made from a specially designed Canna hybridizing program with said hybrid cultivars being planted and grown in Grain Valley, Mo.

ORIGIN AND ASEXUAL REPRODUCTION

Asexual reproduction of this cultivar by dividing the rhizome was directed by me, such reproduction establishing that the plant does in fact maintain the characteristics described, in successive generations.

It should be noted that the plant was initially selected from a Canna planting being grown near Grain Valley, Mo. in a cultivated area and has since been reproduced by dividing the rhizome in the vicinity of Grain Valley, Mo. with the new and distinct characteristics stated herein, found to be maintained through successive generations as before recited.

*Canna generalis* is a group of tropical to sub-tropical herbaceous plants grown primarily for their rapid growth and vivid, flamboyant, summer blooms. They are grown in USDA zones 9–10 as a perennial and in USDA zones 3–8 as an annual. General growth habit includes an erect central (main) stalk with large tropical alternate leaves. This massive plant, usually 24"–96" in height, is topped by a colorful, inflorescent display. They are of easy cultivation in any fertile, moist soil, especially soils high in humus.

The cultivar of *Canna generalis* 'Roblibkey' may further be described as having a number of distinctive characteristics which are enumerated in the succeeding specific description but broadly stated as comprising dwarf growth habit, a pastel yellow color with lime-green hue, long-term bloom display, apple green foliage edged with white margins, large, healthy rhizomes, and ultra dwarf early bloom display. The floral display has flowers of pastel yellow of (PMS#100) with greenish infusion (PMS #394). The bloom period begins at approximately 11 weeks after planting and continues until frost.

I have chosen to identify this new cultivar as *Canna generalis* 'Roblibkey'. This cultivar is being marketed in the United States under the name of Liberty (tm) Keylime.

BRIEF DESCRIPTION OF THE DRAWING

The accompanying photograph shows as nearly true as it is reasonably possible to make the same, in a color illustration of this character, typical flowers and leaves of the new variety. The photographic drawing illustrates the flower form, the novel and distinctive flowers, and the foliage.

In the photograph.

DETAILED DESCRIPTION

Figure 1:
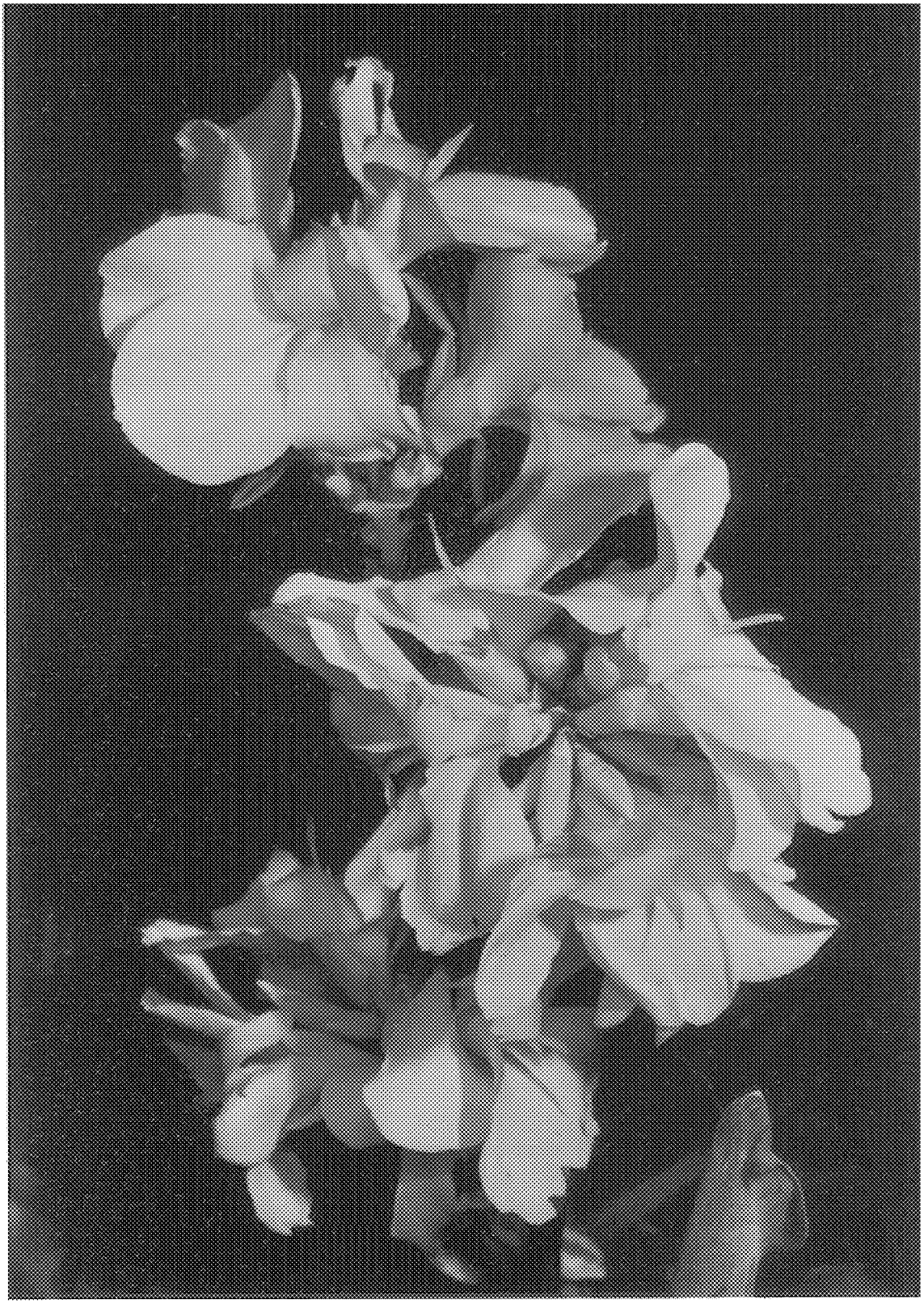
FIG. 1 illustrates the mature flower.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo., unless stated otherwise.

Parentage:

*Seed parent.*—*Canna generalis* hybrid Pfitzer Primrose Yellow (not patented).

*Pollen parent.*—(Same) self pollinated.

Propagation: Asexual reproduction by rhizome division started near Grain Valley, Mo.

Plant descriptions:

*Inflorescence and reproductive parts.*—The overall influorescence is thrysoid (mixed) and is approximately 25 cm in length by 15 cm in width when mature. The terminal axis is indeterminate and the lateral axis are cymose and determinate. The large, zygomorphic, hermaphrodite flowers are borne terminally and more or less erect in a racemose inflorescence and are at anthesis together with one that is in bud. The flowers, borne on short pedicels occur in pairs forming a two-flowered cincinnus. Each flower is subtended by a bract. The outer whorl of the perianth consists of three free, imbricate sepals, the inner whorl of three basically united petals. There are typically three to five petaloid staminodes (showy portion of inflorescence) with the smaller fertile petaloid stamen and style visible at the center of the flower. Colors of "Petals" (showy portion composed of petaloid staminodes): are pale yellow (PMS #100) with greenish yellow (PMS #394). The perianth segments (petals and sepals) are also PMS #394 & PMS #100. Due to the unusual composition of the reproductive parts, self pollination is more common in cannas than is cross pollination. The petaloid stamen and style are visible at the center of the flower. The stamen can be recognized by the presence of the single anther-cell along its upper margin. The pistil is made up of the stigma or tip, the petaloid style and a three locular ovary. The ovary is borne on a short pedicel and each loculus contains numerous anatropous ovules attached to an axile placenta. The rarely formed capsule has a warty pericarp that disintegrates at maturity to release the seeds.

*Terminal axis.*—Indeterminate.

*Lateral axis.*—Cymose and determinate.

*Petaloid staminodes.*—PMS #100 (Pale yellow) and PMS 394 (greenish yellow).

*Perianth segments.*—greenish yellow (PMS #394) & pale yellow (PMS #100).

*Bud at approximately one week prior to opening.*—6 cm to 7 cm which is comprised of: Sepal — 0.6 cm to 1.1 cm; Petal — 1.9 cm to 2.8 cm; and Emerging stamenodes — Varying from 1.4 cm to 3.9 cm.

Color of reproductive parts:

*Anther.*—Dark brown (PMS#476) to black at dehiscence.

*Stigma.*—Translucent cream.

*Ovary.*—Medium green (PMS#361).

*Stamen.*—Pale cream yellow blend, similar to inflorescence.

*Style.*—Pale cream yellow.

*Seeds.*—At maturity are black, and approximately 4 mm by 7 mm in size.

Leaves: The alternate leaves are long ovate in shape and have pinnate veins and a dominate mid-rib. They are large, broad, simple, and entire with sheathing petioles. The average size of leaves at maturity is 45 cm in length by 23 cm in width. The dominate color in young leaves is medium to light green (PMS #367) on both front and back and transitions to medium green (PMS#370) on both front and back at maturity.

Tubers (rhizomes): These tuberous rhizomes are a bone cream in color when immature, and slightly darker cream at maturity. The rhizomes are covered by papery scale-like leaves. This paper-like layering (PMS #439) with darker veining (PMS #440). The average rhizome is 9 cm in length and 2.75 cm in width.

Roots: The fleshy roots arise from the internodes of the rhizomes and vary from 0.09 to 2.9 mm in diameter and are an average length of 26 cm.

Flowering time: The bloom period begins at approximately 11 weeks after planting (when planted at the recommended season and given reasonable care) and continues until frost. No pruning or pinching is required for optimum flowering performance. Spent blooms are shed quickly (approximately 32 hours after opening).

Flower fragrance: No fragance detected.

Diseases: No known unusual susceptibility to diseases noted to date.

Insects: No known unusual susceptibility to insects noted to date.

General Observations

*Canna generalis* 'Roblibkey' with its compact dwarf growth habit, its pastel yellow color with lime-green hue, its long-term bloom display, its apple green foliage edged with white margins, its large, healthy rhizomes, and its ultra dwarf early bloom display is striking in the landscape.

For the purpose of ornamental horticulture in our present living environments which include smaller yards and patio gardening, 'Roblibkey' is ideal due to several characteristics. These plant characteristics are:

A. Unique inflorescence color: The clear yellow-green color of this cultivar has carrying power (visibility) and contrasts the rich green foliage. This color combination is one in high demand by landscapers.

B. Dwarf and compact growth: These characteristics are strongly sought after for the purpose of landscaping with cannas. The hybridizer achieved the desired dwarf and compact growth habit combined with the bloom color desired. The achievement of this is demonstrated primarily by two characteristics: Stem thickness to overall plant height ratio and the internode spacing.

For example: In *Canna generalis* 'Roblibkey', the stem thickness (1⅞") to average height (28") ratio is about 1 to 15.5. In the comparison plant, *Canna generalis* 'Pfitzer Primrose Yellow', the stem thickness (1⅓") to height (36") ratio is 1 to 27. The internode spacing of 'Pfitzer Primrose Yellow' is 6½" and internode spacing of 'Roblibkey' is 5¾" which creates a more dense, compact overall presentation.

This compact and very dwarf growth habit makes 'Roblibkey' ideal for the smaller garden and landscape designs and the patio/pot culture trend.

C. Winter storage: The storage capability of 'Roblibkey' is another characteristic that renders this cultivar advantageous both to home gardeners and to commercial growers. The rhizomes are superior for storage because an average of 95% of stored rhizomes are viable after the winter storage period.

This winter storage capability is very important for two reasons. Since cannas are only grown as perennials in USDA zones 9–10 and must be dug and stored in zones 3–8, a vast majority of home gardeners must routinely dig and store the rhizomes during the winter months. There is great variance as to the ability of different varieties to store successfully. 'Roblibkey' survives winter storage with a high rate of success. Secondly, this storage ability of 'Roblibkey' is of great advantage to commercial canna growers in USDA zones where the cannas must be dug and stored over winter months and a high degree of plant loss renders the product of no marketable value.

D. Early blooming: 'Roblibkey' has the unique tendency to initiate its blooming a week earlier than most other cannas, and to begin an ultra dwarf bloom display at this time. Early color is in great demand, and dwarf and ultra dwarf has excellent popularity in today's market.

Comparison to Known Varieties

The cultivar may be compared with known varieties along the following lines.

*Canna generals* 'Pfitzer Primrose Yellow' is an appropriate choice for a comparision to *Canna generalis* 'Roblibkey' because of the color combination of it's green foliage and yellow bloom. (1) *Canna generalis* 'Pfitzer Primrose Yellow' color presentation is very similar to 'Roblibkey', but the yellow is darker than that of 'Roblibkey' and does not have the lime infusion. (2) 'Roblibkey' is more dwarf than 'Pfitzer Primrose Yellow' i.e., 2–2½ feet in height compared to 3 feet in height for 'Pfitzer Primrose Yellow'. (3) 'Roblibkey' initiates the first bloom cycle approximately one week sooner than 'Pfitzer Primrose Yellow'.

I claim:

1. The new and distinct cultivar of *Canna generalis* plant, substantially as described and illustrated herein, characterized particularly as to novelty by it's compact dwarf growth habit, pastel yellow color with lime-green hue, long-term bloom display, apple green foliage edged with white margins, large healthy rhizomes, and ultra dwarf early bloom display, providing a cultivar well suited as a garden or pot plant having no unuusual susceptibility to the traditional Canna diseases and insects.

* * * * *